(12) United States Patent
Köhler et al.

(10) Patent No.: US 10,169,540 B2
(45) Date of Patent: Jan. 1, 2019

(54) BLOOD GLUCOSE SYSTEM HAVING TIME SYNCHRONIZATION

(75) Inventors: Matthias Köhler, Laudenbach (GB); Peter Blasberg, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1249 days.

(21) Appl. No.: 12/339,968

(22) Filed: Dec. 19, 2008

(65) Prior Publication Data
US 2009/0163793 A1 Jun. 25, 2009

(30) Foreign Application Priority Data
Dec. 21, 2007 (EP) ..................................... 07024884

(51) Int. Cl.
*G06F 19/00* (2018.01)
*A61B 5/00* (2006.01)
*A61B 5/145* (2006.01)
*G16H 40/63* (2018.01)

(52) U.S. Cl.
CPC ........ *G06F 19/3418* (2013.01); *A61B 5/0002* (2013.01); *A61B 5/14532* (2013.01); *A61B 5/4839* (2013.01); *G06F 19/00* (2013.01); *G16H 40/63* (2018.01)

(58) Field of Classification Search
CPC ............. G06F 19/3406; G06F 19/3418; A61B 5/0002; A61B 5/14532; A61B 5/4839; A61M 5/14244; A61M 5/172; A61M 2205/35; A61M 2205/3507; A61M 2205/3523; A61M 2205/3576; A61M 2205/3592; A61M 5/00; A61M 5/142; A61M 5/31568; A61M 2205/33–2205/3303; A61M 2205/3569; A61M 2230/301
USPC ...................... 604/65–67, 131, 151; 600/365
See application file for complete search history.

(56) References Cited

U.S. PATENT DOCUMENTS

| | | |
|---|---|---|
| 4,653,022 A | 3/1987 | Koro |
| 5,536,249 A | 7/1996 | Castellano et al. |
| 5,921,938 A | 7/1999 | Aoyama et al. |
| 5,925,021 A | 7/1999 | Castellano et al. |
| 6,001,082 A | 12/1999 | Dair et al. |

(Continued)

FOREIGN PATENT DOCUMENTS

| | | |
|---|---|---|
| DE | 197 33 445 | 2/1999 |
| DE | 695 34 225 | 1/2006 |

(Continued)

OTHER PUBLICATIONS

European Search Report dated Apr. 21, 2008 including enclosures.

*Primary Examiner* — Theodore Stigell
*Assistant Examiner* — Laura Schell
(74) *Attorney, Agent, or Firm* — Harness Dickey

(57) ABSTRACT

The present invention provides a blood glucose system for treating a glucose metabolic disorder. The system includes a dosing device having a counter for generating a count and memory for storing dose quantities and counts, a blood glucose measuring device having memory for storing blood glucose measurements and measurement times, and a data processor for receiving data from the dosing device and blood glucose measuring device and converting counts to actual times. The data processor synchronizes the counts with the measurement times using a time standard.

13 Claims, 1 Drawing Sheet

(56) References Cited

U.S. PATENT DOCUMENTS

| | | | |
|---|---|---|---|
| 6,216,096 B1* | 4/2001 | Obermeier | 702/177 |
| 6,277,099 B1 | 8/2001 | Strowe et al. | |
| 6,287,283 B1 | 9/2001 | Ljunggreen et al. | |
| 6,482,185 B1 | 11/2002 | Hartmann | |
| 6,540,672 B1* | 4/2003 | Simonsen et al. | 600/300 |
| 6,585,698 B1 | 7/2003 | Packman et al. | |
| 6,997,911 B2 | 2/2006 | Klitmose | |
| 2002/0193679 A1* | 12/2002 | Malave et al. | 600/407 |
| 2003/0220814 A1 | 11/2003 | Gordon | |
| 2005/0038674 A1 | 2/2005 | Braig et al. | |
| 2005/0103351 A1 | 5/2005 | Stomberg et al. | |
| 2005/0177398 A1* | 8/2005 | Watanabe et al. | 705/3 |
| 2005/0192846 A1* | 9/2005 | De Zwart et al. | 705/3 |
| 2007/0066938 A1* | 3/2007 | Iio | A61B 5/1411 604/152 |
| 2008/0281297 A1* | 11/2008 | Pesach | A61M 5/14244 604/890.1 |
| 2008/0319295 A1* | 12/2008 | Bernstein et al. | 600/365 |
| 2009/0024112 A1* | 1/2009 | Edwards | A61M 5/19 604/890.1 |

FOREIGN PATENT DOCUMENTS

| | | |
|---|---|---|
| EP | 1 391 794 | 2/2004 |
| EP | 1 758 039 | 2/2007 |
| EP | 1 762 955 | 3/2007 |
| WO | WO 00/18449 | 4/2000 |
| WO | WO 03/014903 | 2/2003 |
| WO | WO 2005/043306 | 5/2005 |

\* cited by examiner

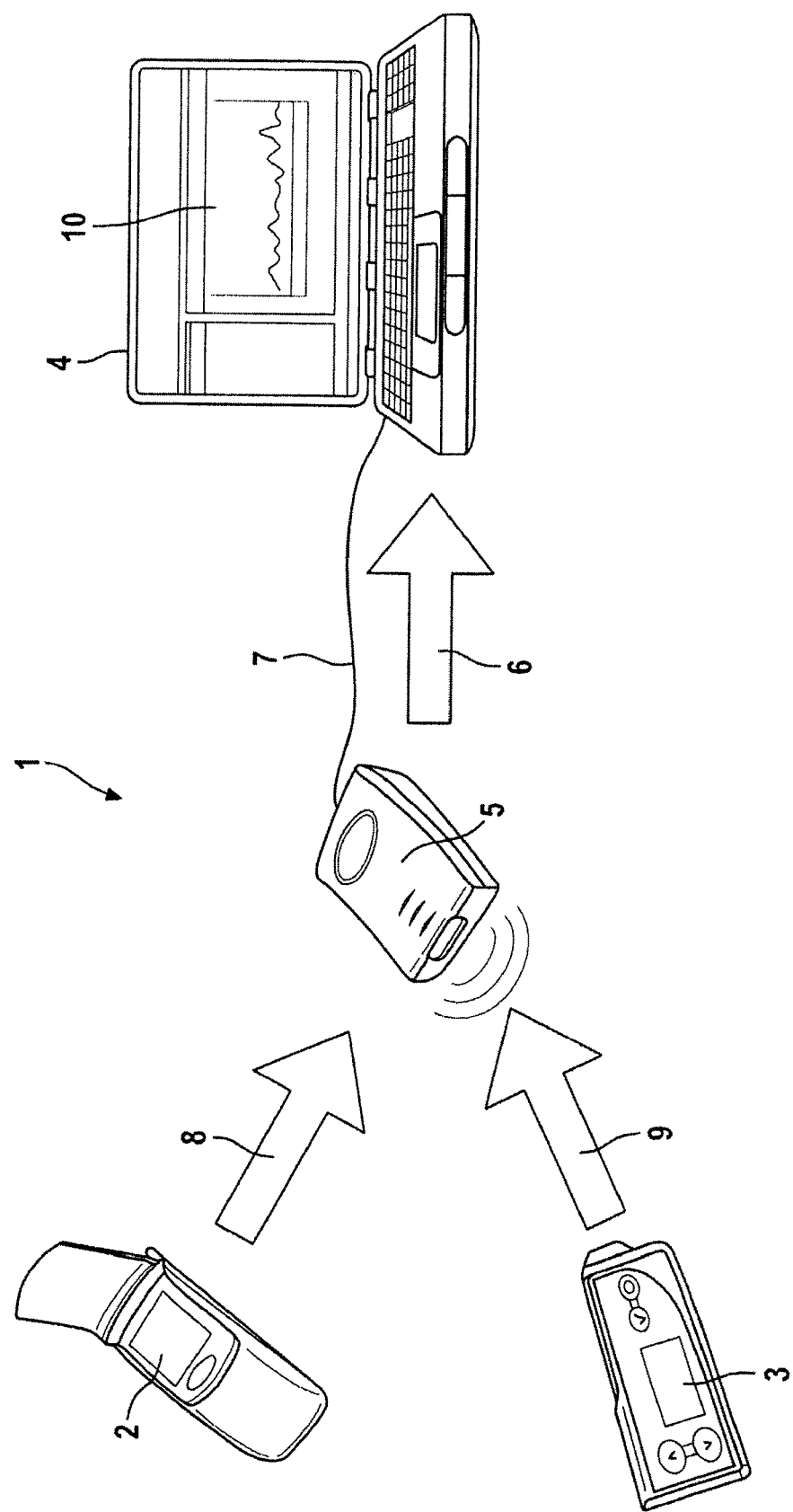

BLOOD GLUCOSE SYSTEM HAVING TIME SYNCHRONIZATION

REFERENCE

This application claims priority to European Patent Application No. EP 07 024 884.4, filed Dec. 21, 2007, which is hereby incorporated by reference in its entirety.

FIELD

The present invention relates to a blood glucose system for treating a glucose metabolic disorder. The system includes a dosing device for delivering a medicinal agent for treating the glucose metabolic disorder to a body, a blood glucose measuring device for determining the blood glucose content of the body, and a data processing apparatus for processing stored data sets of the dosing device and the blood glucose measuring device. The invention is thus directed to devices for the diagnosis or treatment of a glucose metabolic disorder, such as diabetes.

BACKGROUND

The dosing device for delivering a medicinal agent for treating the glucose metabolic disorder to a body is an injection device or an inhalation device, preferably a device for delivering or injecting insulin. Such devices are known, for example, as an insulin pen (for example, from Novo Nordisk Inc. and Johnson & Johnson, Inc.), an insulin pump (for example, from Roche Diagnostics GmbH), or insulin inhalers. Insulin pens are thick sticks having a needle and an insulin cartridge for delivering multiple doses of insulin, whereby a new piercing occurs each time. The number of units of insulin to be delivered upon a piercing is set by a setting wheel. Insulin pen injection devices having an integrated time standard are known from U.S. Pat. No. 5,925,021 and DE 695 34 225.

An insulin pump is a medical device for continuous or interval-type subcutaneous insulin infusion. It is a small infusion device which is worn on the body and supplies insulin to the body continuously or at intervals via a catheter and a needle lying below the skin. The dosing may also be adapted to a specific daily routine or specific events, such as before or after a meal.

A blood glucose measuring device is an analytical measuring device for determining or recording (so-called "electronic diary") a blood glucose value. Such devices are also referred to as blood glucose meters, blood sugar measuring devices, or blood glucose recorders. Blood glucose recorders are devices which record blood glucose concentrations over a predefined period of time, for example, to be able to establish a suitable insulin dosing scheme for a diabetes patient.

A blood glucose measuring device is a device which may determine the blood sugar content. For this purpose, a piercing wound is typically generated in a body, a blood droplet is taken, and the blood glucose content in the droplet is determined with the aid of the blood sugar measuring device. However, it is also conceivable to measure the blood glucose by a permanent measurement, for example, using sensors inserted into the body or by measuring through the skin.

Dosing devices and blood glucose measuring devices are capable of functioning and operating independently, i.e., independently of other connected components or devices. For example, a measuring device delivers measured values or an insulin pump operates without being connected to another device. It also has a separate internal power supply in this case and is operable line-independent.

A data processing apparatus may, for example, be a PDA, a data manager, a communication adapter (see EP 1 762 955), or a PC, which is used to read, store, or display stored data from the dosing device and blood glucose measuring device.

The dosing device in exemplary embodiments comprises an integrated time counter for generating relative time values, a memory unit in which data sets of dosing quantities and associated time values are stored, and a device for transmitting stored data sets to a data processing apparatus. The blood glucose measuring device for determining the blood glucose content of the body comprises an integrated time standard (e.g., a clock), a memory unit in which data sets of blood glucose measurements and associated time values are stored, and a device for transmitting stored data sets to a data processing apparatus. The device for transmitting the data sets may be integrated in the blood glucose measuring device, connected as a separate module thereto, or integrated in the data processing apparatus.

Dosing data from the dosing device and analysis results from the blood glucose measuring device are transmitted together with associated time values from the time counters of the dosing device and blood glucose measuring device to the data processing apparatus and processed therein. The time values are converted into corrected time values by comparing the time values with the time standard. The term "associated time values" means the particular time values at which the associated dosing or analysis occurred are transmitted.

A plurality of portable devices for measuring the blood sugar level is known in the prior art, in which a blood sample is dispensed onto a test element, which is subsequently analyzed using the blood glucose measuring device. Blood glucose measuring devices of this type typically have a memory, in which analysis results and the corresponding time at which the measurements were performed are stored. Furthermore, there are systems in the prior art in which the analysis results of a blood glucose measuring device are relayed or transmitted to an analysis unit. Devices of this type are becoming increasingly more significant in particular in the care and education of diabetics. The diabetic may solely decide whether insulin must be injected on the basis of individual measurements. In contrast, through the acquisition of blood sugar measurements over the course of a day and during multiple days or weeks, the diabetic may obtain information about how his blood sugar level is influenced by ingestion of food, physical activities, and other factors. In addition, the diabetic receives important information about how his body responds to the delivery of insulin by a history of monitoring the blood sugar level.

A diabetes data management system is commercially available from Roche Diagnostics GmbH. The data obtained using a handy blood sugar measuring device is transmitted in this system to a PC, which displays the history of the blood sugar level over time and also allows analyses which provide the patient with indications of the strength of the above-mentioned influencing factors. Systems which provide historical monitoring of the blood sugar level are designed in such a manner that the user first performs a plurality of measurements and transmits the measurement results to an analysis unit at a later point in time. It is therefore necessary to also store the times at which the analyses were performed together with the results in the blood glucose measuring device.

Because both dosing devices and blood glucose measuring devices must operate reliably over a period of time of months or years, it is necessary to either install a clock having a high running precision in the device or to provide a clock that may be set. On the one hand, clocks having high running precision with changing ambient temperatures are still relatively expensive. On the other hand, it is inconvenient for the user to have to set the clock. In addition, setting the clock requires additional operating elements which must be integrated into the device and thus makes it more costly. Moreover, it is also undesirable in many cases that the diabetic can adjust the clock. Specifically, historical monitoring is frequently performed to check whether the diabetic follows the rules and/or instructions provided by the physician. A further aspect are time changes, for example, between summer and winter and upon the change between time zones. Adjusting the clock to the current time may result in the later assignment or adjustment of measured values to absolute times not being possible. For such cases, it may therefore be advantageous to block or prevent adjusting the clock of the device or the time counter.

For more precise and informative history monitoring of a diabetes treatment and optimization of the treatment on the basis of a precise diagnosis, it is necessary to consider not only the data stored in the blood glucose measuring device, but also to register the insulin doses administered by the dosing device precisely and compare them to the measured values. It is also important to be able to optimize the therapy on the basis of an analysis. For this reason, the dosing devices used in the corresponding systems also have a memory apparatus for storing data.

Therefore, this requirement results in the analysis of the data from the dosing device and the blood glucose measuring device to allow a time registration of both the history data stored in the dosing device and blood glucose measuring device and also to assign the data registered by the dosing device and the blood glucose measuring device to one another in regard to time, i.e., to synchronize them in regard to time. Accordingly, this compensates for errors and deviations in the time registration and allows the data to be analyzed using the same correct timescale. This effort should be kept as simple as possible.

A system having a dosing device, a blood glucose measuring device, and a computer for displaying history data, as well as a communication adapter connecting the dosing device and the blood glucose measuring device to the computer, is known from EP 1 762 955. Both the dosing device and the blood glucose measuring device have a time standard, i.e., a clock, and the storage of a data set in the devices includes the associated clock time. On one hand, this requires more effort, and also the problem of time synchronization and assignment of history data is not solved for the case of unavoidably occurring deviations between the clocks in the two devices. The history data received by the computer and/or the communication adapter is unchanged and without time adjustment.

An infusion pump is disclosed in EP 1 115 435, which may be connected to a computer to read data. The clock times in the infusion pump and the computer are compared, and if a deviation occurs, the user is requested to reset the time in the clock. (See ¶ [0039]). The clock in the infusion pump is implemented by a counter which starts when the device is produced and is set to an absolute time. (See ¶ [0110]). The current clock time of the insulin pump then results from the start time and the number of count pulses passed since then. A corresponding implementation of an integrated time standard in a portable electrocardiogram recorder is described in U.S. Pat. No. 4,653,022.

A portable, independent ambulantly operable blood glucose measuring device for determining the blood glucose content of a sample of body fluid is disclosed in document DE 197 33 445 and U.S. Pat. No. 6,216,096. The device comprises an integrated time counter for generating relative time values, a memory unit in which data sets of blood glucose measurements and associated time values are stored, and a device for transmitting stored data sets to a data processing apparatus.

Document WO 2005/043306 describes a time synchronization system in an apparatus for emergency monitoring, in which all system components comprise an integrated time standard, i.e., a clock. This document teaches the synchronization of different medical devices used in emergency medicine, such as physiological monitors and defibrillators, each of which comprise a separate integrated time standard. These devices used in emergency medicine are typically large and costly such that an integration of a precise clock or a comfortable, clearly arranged operating unit is not considered a significant cost. In contrast, in a blood glucose system for treating a glucose metabolic disorder, both costs and size play a significant role. In addition, the devices of a blood glucose system to which the invention is directed are not operated by trained qualified personnel, as with emergency-medicine devices, but rather by laypersons who cannot be expected to operate complex devices, in particular because diabetes patients are frequently restricted in their manual capabilities.

SUMMARY

The present invention is directed to the concept of time management in a blood glucose system having a dosing device, such as an insulin pen, and a blood glucose measuring device working together with the dosing device, in which the time of registration and integration of dispensing, e.g., the time of injection of the dosing device with the corresponding times of blood sugar measurements is implemented.

A blood glucose system is provided in which the obtained blood glucose measurement results may be assigned or adjusted as exactly as possible to the time of analysis and the times of the associated dosing deliveries, and in which both costly precision clocks and operating elements for setting clocks may be avoided. Thus, the devices may be cost-effective, small, and easily operable.

An exemplary embodiment of a blood glucose system for treating a glucose metabolic disorder includes a portable, independent ambulantly operable dosing device for delivering a medicinal agent for the treatment of the glucose metabolic disorder to a body. The dosing device comprises an integrated time counter for generating relative time values (e.g., counts), a memory unit in which data sets of dosing quantities and associated time values (e.g., counts) are stored, and a device for transmitting stored data sets to a data processing apparatus or processor. The system also has a portable, independent ambulantly operable blood glucose measuring device for determining the blood glucose content of the body. The blood glucose measuring device includes an integrated time standard (e.g., clock), a memory unit in which data sets of blood glucose measurements and associated time values (i.e., measurement times) are stored, and a device for transmitting stored data sets to a data processing unit. The system further includes a data processing unit for processing data sets transmitted from the dosing device and the blood glucose measuring device. The unit has a receiving device for receiving the data sets from the dosing device and the blood glucose measuring device and an arithmetic unit for converting the time values (counts) of the data sets of the dosing device into absolute time values (i.e., actual times) by comparing the time value of the time counter of the dosing device to the time value of a time standard (e.g., a clock).

The data processing unit is implemented to synchronize the data sets or of the dosing device and the data sets of the blood glucose measuring device with one another using the time value of the time standard by an assigned linkage.

An advantage of this embodiment is that the portable, independent ambulantly operable dosing device, such as an insulin pump or insulin pen, does not require a precise time standard, i.e., an expensive clock having a high running precision. Instead, the dosing device only has an integrated time counter for generating relative time values or counts and thus it is sufficient if another system component, such as the blood glucose measuring device or the data processing apparatus, contains an integrated time standard, e.g., a precisely-running clock. Furthermore, no operating elements must be provided on the dosing device for setting the time on a clock. The system is thus cost-effective, has a compact construction, and simplifies the operation for the user.

Relative time values include time data which are registered in relation to a reference instant (i.e., an instant in time), the reference instant in turn being able to be a relative instant or an absolute instant. A time standard, in contrast, is a clock which does not provide a relative time, but rather an absolute or actual time. An integrated time standard is a clock which is installed as a component in a particular device.

In one embodiment, a dosing device has a time counter which is relatively simple with regard to its operating precision. Furthermore, the dosing device is equipped for storing data sets of dosing deliveries (e.g., dosing quantities) and time values (e.g., counts). The blood glucose system also contains a data processing apparatus or data processor and a time standard, which may be located in the data processor or the blood glucose measuring device. By comparing the relative time value or count generated from the time counter to the actual time of a clock (i.e., the time standard), the time value or count may be converted to an absolute or actual time and thus the stored dosing history data may be assigned absolute or actual time values. In this manner, cost-effective time counters may be used in the dosing device, and an assignment or adjustment of the stored history data of the dosing device to comparatively exact times is possible. Furthermore, errors due to a misaligned or misadjusted time counter are reduced, and operating elements are saved on the dosing device.

For example, typical quartz pulse generators or electronic shift registers may be used as the time counter in the dosing device. It is usually unimportant whether the time counter provides a clock time or simply the count of a shift register. However, it is important that the time counter not have excessively large running inaccuracies. The pulse rate of the time counter should be as constant as possible and known in advance, however, so that the differences of various counts may be converted into time differences or absolute times. This may be performed according to the following formula: $tA=tD-(nD-nA)/v$. tA is the absolute time, at which a dosing A was performed. The following are necessary for its calculation according to the above formula:

tD: time of data transmission, i.e., time at which the time value of the time counter and clock time of the time standard may be compared;

nD: count of the time counter upon comparison to the time standard (typically upon data transmission)

nA: count of the time counter which was stored at the instant of the dose delivery; and v: pulse rate of the time counter, for example, in counting units (clock pulses, counting pulses, counting steps) per minute.

The pulse rate (counts per time unit) is known and the data processing apparatus is programmed in such a manner that it takes this pulse rate into consideration or the pulse rate is transmitted from the dosing device to the data processing apparatus. However, the pulse rate may also be ascertained by the data processing apparatus. For this purpose, two or more data transmissions at different times from one another are used: $v=(n2-n1)/(t2-t1)$.

A difference between counts (n2−n1), which is calculated from two counts, is divided by the associated difference of the actual times of the time standard (e.g., clock). Associated means that t1 and n1 and t2 and n2 were each ascertained at the same real instant of time (i.e., t1 and n1 occurred at the same time and t2 and n2 occurred at the same time). The t1 differs from t2, the more precisely the pulse rate v may be ascertained. The pulse rate ascertainment may be performed without additional effort, if t, n value pairs of one or more preceding data transmissions are stored and the pulse rate calculation is performed upon a further data transmission in consideration of stored values and the current t, n value pair. The present invention provides independence in the ascertainment of absolute time values for dosing deliveries from an offset (i.e., an adjustment) of the time counter. The time counter begins to run with the application or contacting of an operating voltage. The user of the dosing device may also set the time counter. However, the user preferably does not have any influence on the time value of the time counter.

In a different embodiment, a time counter may be used which begins to run when connected to a battery. The status of the time counter is relayed to a conversion unit, which ascertains a clock time from this value, and is displayed on the display. The user may be given the ability via operating buttons of performing reprogramming of the conversion unit or, in other words, setting the clock. However, the value of the time counter remains unaffected by the intervention of the user, so that no error is induced in the calculation of the absolute times of the dosing deliveries by setting the clock. For example, if the user performs measurements for winter time and then changes the clock over to summer time, this has no influence on the time counter and a unique assignment or adjustment of the history data to absolute times is still possible.

The dosing device may advantageously have a conversion unit, which converts time values of the time counter into absolute time (e.g., clock time), and the conversion unit may be reprogrammed by the user and/or by the data processing apparatus to correct the clock time.

For the monitoring of blood glucose data, it is advantageous to record a plurality of data sets which contain dosing deliveries and/or blood glucose values and associated time values. A dosing device and blood glucose measuring device thus require a memory unit for storing one or more data sets. Commercially available devices are typically already equipped with memory of this type. Furthermore, the devices also have a device for transmitting stored data sets to the data processing apparatus. In commercially available systems, data transmission is implemented via plug connections and cables. Furthermore, it is also possible to implement a wireless data transmission, e.g., via an optocoupler (IR) or by radio (Bluetooth, RF).

A very simple data transmission which is easily operable for the user is possible if the device contains a transmitter which transmits data to the data processing apparatus without mechanical coupling having to be performed. An electrical separation of measuring device and data processing apparatus is thus achieved. This may be implemented, for example, by an infrared diode in the device and a corresponding infrared detector in the data processing apparatus, as is known from remote controls for televisions. The data transmission occurs via modulated light in such an embodiment. It is advantageous if the data transmission is not performed only unidirectionally from the device to the data processing apparatus, but rather if the data processing apparatus in turn also contains a unit for transmitting data to the device, so that bidirectional communication between the units is possible. This may advantageously be used so that the data processing apparatus first reacts to the device and requests data. After completed data transmission, the data processing apparatus may confirm receipt, so that it is ensured that the data exchange has occurred completely.

A data processing apparatus for processing data may be implemented, for example, as a personal computer having corresponding software. The data processing apparatus may also be a handy unit, however, which corresponds to a notebook, notepad, palmtop, or the like. The data processing apparatus contains a processing unit (CPU), a memory unit, and preferably a display for displaying analysis results.

The processing of data by the data processing apparatus may also include calculations, such as when the dosing deliveries or analysis results are converted into other units, for example. An important aspect of the processing of data may also be with its graphic display, the ascertainment of trends, and the correlation of influencing variables to changes in the results. The processing of the results may therefore be performed, for example, in a form which gives a diabetic information about how he must behave and which insulin doses he must inject to obtain the most uniform possible blood sugar level that lies in a standard range. The data processing apparatus has a device for receiving data sets from the dosing device and blood glucose measuring device. As already described above with the dosing device, a device of this type may be implemented via electrical supply lines or via radio receiver or optical receiver.

In the assignment or adjustment of data from the dosing device and blood glucose measuring device, the data processing apparatus considers a time standard or clock which is used as a reference to convert the time values of the dosing device into absolute time values. The time standard or clock may be implemented in the blood glucose measuring device or in the data processing apparatus or in both. Accordingly, in a first advantageous embodiment, measurement times stored within the blood glucose measuring device may be used for linking the data sets (i.e., counts) of the dosing device and the blood glucose measuring device. In a second advantageous embodiment, the data processing apparatus includes an integrated time standard or clock, and the measurement times from the blood glucose measuring device or the time values from the clock of the data processing apparatus are used for linking the data sets of the dosing device and the blood glucose measuring device. Alternatively, a combination of the time values from both clocks (time standards) may be used.

Absolute or actual time values do not have to be absolutely correct; instead, this term is to be understood in contrast to the time value of the time counter, which may be a number or a completely incorrect clock time such that converting the time values of the time counter to a clock time (and a date) is performed and offsets and running inaccuracies are corrected. For example, quartz clocks having high running precision and radio clocks are suitable as the time standard. The quartz clocks normally contained in computers do not have especially high running precision, but may be set easily by the user. The clock or time standard may also be obtained from a time server via radio or data connection (e.g., via the Internet).

Setting the clock or time standard is less disadvantageous for several reasons than having to set the time registration in the dosing device. First, setting the clock or time standard may be performed simply and comfortably via a keyboard. If necessary, the data processing apparatus may typically be placed under the control of an attending physician or adviser, so that manipulations are avoided. Moreover, in practice, not every user of an analysis device typically has their own data processing apparatus, but rather the users of an analysis device go to their attending physician or adviser who has the data processing apparatus. One data processing apparatus may therefore be used to process the data of many different blood glucose systems. Therefore, only one single clock or time standard which must be monitored is necessary for this plurality of blood glucose systems.

The present invention also relates to a method for processing analysis results using a blood glucose system for treating a glucose metabolic disorder. The blood glucose system includes a portable, independent ambulantly operable dosing device for delivering a medicinal agent for the treatment of the glucose metabolic disorder to a body. The dosing device includes an integrated time counter for generating relative time values or counts, a memory unit in which data sets of dosing quantities and associated time values or counts are stored, and a device for transmitting stored data sets to a data processing apparatus. The system also includes a portable, independent ambulantly operable blood glucose measuring device for determining the blood glucose content of the body. The device comprises an integrated clock or time standard, a memory unit in which data sets of blood glucose measurements and associated time values are stored, and a device for transmitting stored data sets to a data processing apparatus. The system further includes a data processing apparatus for processing data sets of the dosing device and the blood glucose measuring device. The apparatus includes a receiving device for receiving data sets transmitted from the dosing device and the blood glucose measuring device and an arithmetic unit for converting the time values of the data sets (e.g., counts) of the dosing device into absolute values (i.e., actual times) based on a comparison of the time value of the time counter of the dosing device to the time value of a clock or time standard. The data processing apparatus is implemented to synchronize the data sets of the dosing device and the blood glucose measuring device to one another using the time value of the clock or time standard via an assigned linkage.

The method includes storing one or more data sets in the dosing device related to deliveries of a medicinal agent for the treatment of the glucose metabolic disorder performed using the dosing device. The data sets include dosing quantities and time values or counts which were obtained using the integrated time counter at the instant of the particular delivery. The method also includes storing one or more data sets of blood glucose measurements using the blood glucose measuring device. The data sets contain analysis results and measurement times which were obtained using the integrated clock or time standard at the instant of the particular measurement. The method further includes transmitting one or more data sets stored in the blood glucose measuring device and the dosing device to the data processing apparatus and transferring the time value or count of the time counter of the dosing device to the data processing apparatus.

The absolute or actual time values are then calculated at which the agent was delivered by the dosing device using the data processing apparatus from the time values of the data set (i.e., counts) of the dosing device by comparing the current time value (count) of the time counter of the dosing device to the actual time of a clock or time standard. The data sets of the dosing device and the data sets of the blood glucose measuring device are synchronized with one another using the time value of the clock or time standard via an assigned linkage. The method includes processing the dosing quantities and analysis results on the basis of the calculated time values.

The step of processing the dosing quantities and analysis results may be understood in the broadest meaning as the storage, transmission to a data processing apparatus, or display of the synchronized data sets of the dosing device and the blood glucose measuring device. The manner of operation of the method is explained on the basis of the following example.

When the time counter is contacted by an operating voltage, it begins to run at a constant and known in advance pulse rate. A first dosing is performed by the user using the dosing device at instant T1 and a corresponding data set is stored, which comprises the delivered dose quantity and the associated time count. Some time later, the user goes to his physician, where a transmission of the data set to the data processing apparatus is performed at instant T2. Together with the dose value and the associated time value, the current time value of the time counter (i.e., the time value at data transmission) is also transmitted to the data processing apparatus by the dosing device. In addition, data sets of the blood glucose measuring device are also read or downloaded by the data processing apparatus.

The data processing apparatus calculates the difference between the current time value of the time counter (at the time of transmission) of the dosing device and the associated relative time value of the time standard. Upon a subsequent analysis of the history of data stored in the dosing device, the relative time values of the data sets are converted by subtracting the time difference into absolute time values. It is clear that the time values or counts of the time counter and the clock or time standard which are used for calculating the time difference must represent the same real instant or time. Therefore, the current time value or count of the time counter is transmitted to the data processing apparatus for calculating the difference and the time value of the clock or time standard provided at the instant of data transmission is used. A time difference or correction value is calculated from the time value of the clock or time standard at a specific instant and the time value of the time counter at the same instant. The time values of the data sets are then adjusted or converted into absolute or actual times by adding the time difference.

In another advantageous embodiment that uses data transmission, synchronization may be performed between the data sets downloaded from the blood glucose measuring device and the dosing device, i.e., the data may be converted along with the data from the dosing device to a uniform and commonly precise absolute time and assigned or adjusted with respect to one another. Furthermore, the time counter in the dosing device may be reset or the status of the time counter and the associated time of the time standard is stored therein such that this data pair may be used as a new calculation basis for converting time values into absolute times. In this manner, offsets in the time counter and running inaccuracies which have occurred before synchronization no longer influence time calculations which occur after synchronization.

The advantages of an exemplary blood glucose system may be recognized more clearly on the basis of the following table:

TABLE 1

|  | Time counter | Time standard | Line |
|---|---|---|---|
| Factory setting | June 15, 2002 9:30:00 | June 15, 2002 9:30:00 | 1 |
| Dose delivery I | July 15, 2002 8:40:00 | July 15, 2002 8:45:00 | 2 |
| Transmission | July 17, 2002 10:25:00 | July 17, 2002 10:30:20 | 3 |
| Transmission | January 15, 2007 9:30:00 | January 15, 2007 15:00:00 | 4 |
| Dose delivery II | January 16, 2007 9:30:00 | January 16, 2007 15:00:10 | 5 |
| Transmission | January 22, 2007 10:00:00 | January 22, 2007 15:31:10 | 6 |

A time counter of a dosing device which loses approximately 10 seconds/day was used in the above table. Line 2 of the table shows that upon a first dose delivery one month after setting the time counter, a time difference from the clock or time standard (in the blood glucose measuring device or the data processing apparatus) which specify or contain the correct absolute time of 5 minutes already occurs. If the patient goes two days later to his physician and the data sets are transmitted in connection with the data sets of the blood glucose measuring device, the system recognizes a time difference between the time counter and time standard (e.g., clock) of 5 minutes and 20 seconds. A simple addition of this difference to the time value for the dose delivery I already reduces the time difference from 5 minutes to one of 20 seconds. However, if the system is used for monitoring blood sugar levels, a time difference of 5 minutes is significant for most historical evaluations. Therefore, a measurement 5 years after setting the time counter is shown in Table 1. Line 4 of Table 1 shows that according to a dose delivery on Jan. 15, 2007, a time difference of four hours already exists between the time values of the data sets stored in the dosing device (e.g., from the time counter) and the time values of the data sets stored in the blood glucose measuring device. If dosing values and analysis results in the year 2007 were analyzed without correction, a history of monitoring blood sugar levels would fail completely because a blood sugar level measured midday would be interpreted as a measured blood sugar level in the morning.

A second dose delivery according to line 5 of Table 1 may be corrected easily in regard to the time values if, during the transmission of the data sets, i.e., the next transmission of stored data sets from the dosing device to the data processing apparatus, the time difference between the time counter of the dosing device and the clock or time standard is calculated and the calculated time difference is used immediately or at a later instant to correct the time values of the data sets stored in the dosing device. For example, upon a first data transmission, a first time difference between the clock or time standard and the time counter may be calculated. During a second data transmission, a corresponding second time difference is calculated and time values lying between the two data transmissions may be ascertained by interpolating between the first and second time differences and adding the interpolated time difference to the time value of each dose delivery. For example, if a transmission is performed on Jan. 22, 2007, the time difference is calculated as 5 hours, 31 minutes, and 10 seconds by adding this time difference to the time value of the time counter on Jan. 16, 2007 (see column 5), the inaccuracy or time difference may be reduced to 1 minute, which is acceptable for normal history monitoring of blood glucose levels.

For evaluations at a specific instant, correction of the time value of the time counter may advantageously be ascertained by interpolation of running inaccuracies, which were found upon transmission before and after the measurement. For example, it may be ascertained from the data shown in lines 4 and 6 of Table 1 above that an inaccuracy of 70 seconds has occurred within 7 days. It may be concluded that the inaccuracy ascertained on Jan. 15, 2007 has had an additional 10 seconds of inaccuracy added at the date of the analysis (line 5). However, because in practice time inaccuracies are not constant, but instead are caused by differences in temperature and other related factors, the precision achieved by interpolation is limited.

The dosing device has a relative time or count and the blood glucose measuring device has an absolute or actual time. The data processing apparatus may or may not have a clock or time standard. If the data processing apparatus has no clock, it receives the actual time from the blood glucose measuring device, converts the data from the dosing device therewith, and thus generates a common data set between the data from the dosing device and the blood glucose measuring device for display. If the data processing apparatus has a clock or time standard, the clock or time standard of the data processing apparatus may additionally or alternatively be used.

Insulin delivery using the dosing device may be triggered by the user at an arbitrary instant or may also occur at a fixed frequency, for example, once per minute. The dosing quantities are stored in this fixed sequence in the memory of the dosing device and the memory pointer is increased by one. Upon readout or download of the data by the data processing apparatus, only the current memory pointer, the associated measured value, and the measured values stored before it are transmitted, but without their pointers. To reconstruct the history of data, the data processing apparatus assigns the absolute time instant to the current measured value, namely, the time instant of data transmission, based on the clock or time standard of the blood glucose measuring device, the data processing apparatus, or a combination of both. The data processing apparatus then stores the dosing value with the absolute or actual time in the memory of the data processing apparatus. The preceding dosing values are stored without time values in the dosing device. The time reference at the instant of data transmission to the data processing apparatus is in turn provided via a time rule and the memory pointer in the dosing device. Memory space is saved in this manner. The condition wherein absolute time may be assigned to a specific data set is such that the data processing apparatus accesses the dosing device at least once in the corresponding time interval and the data is transmitted.

The dosing device has automatic data collection and data storage having a time marking on a relative time basis. This may be performed in a permanently predefined time interval of the individual dosing or measuring points or may be triggered by the user on the basis of his subjective sensitivity.

A quartz may generate a time signal, for example, from which a microcontroller derives a precise time interval. With a time counter implemented in this manner, for example, a data set is generated each minute and stored consecutively in the memory. A convention within the system then makes the time assignment occurring in the data processing apparatus possible via the knowledge of the memory address. A difference from a blood glucose recorder, i.e., a blood glucose measuring device having history measurement which also has a time controller, is that in such a blood glucose recorder which measures at predefined time intervals, the time instants of the blood glucose measurement are triggered using the time counter, i.e., the time counter is the trigger triggering the measurement and the chronological assignment of the measurement is made possible via the memory space address. In a dosing device, in contrast, the user performs a delivery of insulin at any instant and a count is then assigned to this dosing delivery. The triggering is thus performed by the user and the time counter allows the chronological assignment of the dosing delivery to a time.

Thus, in a blood glucose recorder, measurement is performed using a fixed measuring frequency of 1 Hz, for example, and the measured values are stored in a fixed sequence in the memory. Upon readout, only the memory space index and the measured value have to be transmitted to be able to reconstruct the history. A time counter is thus not necessary in a blood glucose measuring device. By contrast, in a dosing device, the instant time value and frequency of the dosing deliveries are unknown. Therefore, at least one relative chronological assignment of the dosing deliveries must also be stored in the data sets, to allow a chronological history assignment of the previous dosings. A time standard or, to simplify the apparatus, a time counter may be used for this purpose.

The time counter is used for the chronological assignment of the data (boli) stored in the dosing device to the blood glucose measured values of the blood glucose measuring device if the data of the dosing device and the blood glucose measuring device are displayed jointly in or on the data processing apparatus or a device connected to the data processing apparatus. This data can be displayed in a graph or adjacent to one another in multiple graphs. The relative chronological assignment of data from the dosing device to the data from the blood glucose measuring device has to be ascertained and considered. In one embodiment, a clock or time standard is not integrated into the dosing device, but rather a time counter is used for the relative time registration. For this purpose, a time generator or a counter is integrated into the dosing device which counts up or down in a fixed cycle. For each delivered bolus, the associated count of the time counter is stored. Upon reading the history of data stored by the dosing device and the blood glucose measuring device, the current time of the time standard used, i.e., from the blood glucose measuring device, the data processing apparatus or a combination of both is taken as the starting time and assigned to the current count. Starting from this current count, boli stored earlier in time are then assigned or adjusted to absolute or actual times. Advantages with this procedure include the fact that no time synchronization is necessary between the dosing device and the data processing apparatus and no time need be set on the dosing device.

The history of data stored in the dosing device may also be displayed in graphic form by the data processing apparatus using only a relative time axis; otherwise, the time reference point is predefined by the user or the time standard (clock), i.e., the blood glucose measuring device or the data processing apparatus.

The period of time which has passed since the last bolus or the last boli may be indicated on the dosing device. Such a relative time specification will suffice for most users or even be more desirable than an absolute specification of the time of the last bolus, because in such a case, the user must first calculate the period of time which has passed using current clock time.

A further advantage of this embodiment is that even if the time of the dosing device is incorrect, the relative assignment of the data of the dosing device to those of the blood glucose measuring device remains correct and no misinterpretation of the combined data occurs, at least as long as no time adjustments are performed in the blood glucose measuring device, which remain unknown if they are not marked. Limiting the runtime of two years prescribed for insulin pens may also be monitored and registered by the time counter, without an absolute clock being required for this purpose.

Furthermore, the time counter in the dosing device may also be used for generating and displaying a current clock time on the dosing device. During production of the dosing device and at a specific count of the time counter, e.g., at count zero, the current absolute or actual time is stored therein and the absolute time may then be calculated from the count for other later instants of time. This may be expedient for various applications, for example, such as the following: 1) For displaying the current clock time in the display of the dosing device. 2) Upon transmission of the data sets from the dosing device to the data processing apparatus, without a time standard (from the blood sugar measuring device or the data processing apparatus) being available, an at least orienting correct time axis may be defined. 3) The data of the dosing device and the blood glucose measuring device may be synchronized and it may be checked whether the current time corresponds on both devices. 4) Upon each communication with a data processing apparatus, for example, upon transmission of the data to the data processing apparatus, the dosing device may request the absolute time of the data processing apparatus (such as the PC time) and thus further calibrate the chronological assignment to the count of the time counter in the dosing device. 5) Worldwide time synchronization, the time counter being calibrated to a worldwide synchronized standard time upon its installation in the dosing device and, upon readout of the time value, being converted back into the worldwide synchronized standard time and from there into the local absolute time.

Fundamental advantages of a time registration integrated into the dosing device include that the duration of an injection may be registered. This registration in the data set of the dosing device is performed, for example, in such a manner that the beginning and the end of a dosing delivery are marked in the data set for associated time values. Upon readout of the data set in the dosing device for display using the dosing device or upon readout of the dosing device using a data processing apparatus, not only are the particular injection instants available for analysis, but rather also the associated injection durations. Depending on the design of the dosing device, the injection duration may contain information about the injection speed and/or the dosing quantity. Furthermore, it may be displayed on the display of the dosing device how slowly the dosing is to be performed, or an injection which is too rapid, in which the insulin sprays past the piercing point or comes back out, may be recognized as a possible error source upon a data analysis.

The injection speed, the so-called "flow," may be determined from the insulin quantity and the injection time. A recommended quantity-dependent injection time may be displayed on the display using this information, for example, by a countdown, or upon data analysis, an injection which is performed too rapidly may be recognized as a possible error source.

If an additional needle sensor is installed, which registers whether the needle used is located in the body during the delivery of agent, e.g., a mechanical feeler or an electrical conductivity measurement of the needle, it may be indicated on the display of the dosing device how long the needle is to remain in the body after the injection. A time period of approximately 10 seconds is recommended for this purpose. It may be registered and/or stored in the data set of the dosing device how long the needle actually remained in the body to recognize deviations as a possible error source in the data analysis. Such a needle sensor may also be used as a priming sensor; when a bolus is delivered without the needle being injected into the body, the bolus is evaluated as priming and is not indicated as the last bolus on the display of the dosing device or in the graphic representation using the data processing apparatus. The stored data set is marked accordingly.

Priming refers to checking the insulin flow to prepare the insulin pen before the injection. In the event of storage of an open insulin cartridge having an attached needle tip and before the first use of a new insulin cartridge, there may be air bubbles in the cartridge and/or the needle tip, because of which the insulin dose set on the insulin pen is possibly not delivered completely. During priming, the insulin pen is held with the injection needle upward. The insulin cartridge is tapped carefully several times using a finger, so that any air bubbles present rise upward. The dose indication is set to four units for a new cartridge, for example, and to one unit for an open cartridge. The set dose is delivered vertically into the air. An insulin droplet must exit from the needle tip, i.e., the air is completely removed. If this is not the case, the dose delivery is repeated until an insulin drop exits from the needle tip. Furthermore, the cartridge change may be interpreted and thus the cartridge usage duration, such as the mean duration, the deviations therefrom, etc., may be displayed, stored, and analyzed.

Methods for analyzing results may be improved in that one or more checksums are transmitted to the data processing apparatus together with the transmitted data sets, which permit a check of whether the data transmission has occurred error-free. Furthermore, it is advantageous if a device-specific identifier of the dosing device and the blood glucose measuring device is also transmitted, so that the data processing apparatus may differentiate between various analysis devices. It was already described above that it is frequently the case in practice that several users go to a physician or adviser with their own dosing devices and blood glucose measuring devices to have an analysis performed there using a data processing apparatus. If an identifier of the particular devices is used, mix-ups may be avoided.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawing, wherein:

FIG. 1 is a schematic of the components of a blood glucose system.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

FIG. 1 shows components of a blood glucose system 1, comprising a dosing device 3 in the form of an insulin pump (or alternatively, for example, an insulin pen or an insulin inhaler), a blood glucose measuring device or blood glucose meter 2, and a data processing apparatus or data processor 4. A communication adapter 5, to which the dosing device 2 and the blood glucose measuring device 3 are connected, is provided as an additional device. The manner of operation of the optional communication adapter 5 is described in EP 1 762 955. The dosing device 3 and the blood glucose measuring device 2 are portable, line-independent medical devices which are used in combination with one another. Both devices have an interface for transmitting and/or receiving data, which can be, for example, implemented as an infrared interface.

The blood glucose measuring device 2 operates using test elements which are inserted into a chamber of the device. The blood glucose measuring device 2 also has operating elements and a display for displaying analysis results. A memory unit, which is integrated within the blood glucose measuring device 2 and is used for storing data containing the analysis results and associated measurement times, is of significance. In addition, the blood glucose measuring device 2 has a time standard or clock which relays time values related to instantaneous analysis results to the memory unit. Furthermore, the blood glucose measuring device 2 has a wired or wireless interface for communicating with the data processing apparatus or data processor 4.

The dosing device 3 may deliver insulin doses to a body. It also has operating elements and a display for displaying functional parameters. An integrated memory unit within the dosing device 3, which is used for storing data such as dosing quantitiess and associated time values or counts, is of significance. In addition, the dosing device 3 has a time counter which relays time values or counts associated with an instantaneous dosing to the memory unit. Furthermore, the dosing device 3 has a wired or wireless interface for communicating with the data processing apparatus 4.

The communication adapter 5 is connected to the data processing apparatus or data processor 4 via a transmission cable 7 for wired data transmission 6. The data processing apparatus or data processor 4 can be a computer such as, for example, a personal computer, a laptop, a handheld computer, a computer in an Internet café, in a doctor's office, at home, or in a pharmacy, whereby the user of the system 1 must only provide devices 2, 3 or devices 2, 3 and the communication adapter 5. The data processing apparatus or data processor 4 optionally contains a time standard (e.g., a clock) in addition to a computer unit.

To read data from devices 2, 3 using data transmissions 8, 9 and displaying the data on the monitor 10 of the computer 4, the communication adapter 5 is first connected to the computer 4 using transmission cable 7. The communication adapter 5 may also be integrated in the computer, however, and data transmission may occur directly from devices 2, 3 to the computer 4.

The dosing device 3 does not have a clock, i.e., no absolute or actual time, but instead only a time counter. The time counter is a pulse generator, i.e., a time difference standard, having a memory in the form of a table. The data sets stored in the table each comprise the number of ticks (pulses) or counts of the time counter which have passed since the last insulin delivery and the delivered insulin quantity, but it does not include the instant (e.g., clock time) or actual time at which the insulin delivery occurred.

The data can be downloaded from the dosing device 3 to the data processing device or data processor 4. The data processing device or data processor 4 has a time standard (e.g., a clock) available, either via an integrated time standard or a time standard from the blood glucose measuring device 2, and thus the absolute or actual time is available. Once the data is downloaded from the dosing device 3, the download instant, also referred to by the data manager as the absolute time, is used to back-calculate the absolute instants (e.g., absolute time) at which the insulin deliveries occurred from the stored number of ticks (pulses) or counts. However, it may also be possible if the download instant is stored, for example, in the communication adapter 5, and the back calculation to the dosing instants first occurs in the data processing device or data processor 4.

If it turns out during the data processing that the clock in the data manager deviates from the actual time, for example, by a comparison to the time of the PC 4, which is synchronized with the absolute or actual time via the internet in many cases, this systematic deviation of the clock of the data manager may be taken into consideration easily by a corresponding correction shift.

An advantage of the time counter in the dosing device 3 is that, in contrast to the prior art, no synchronization has to be performed between a clock of the dosing device 3 and a clock of the data manager. Therefore, the possibility does not remain open as to which of the two clocks has priority in case of deviation or how the deviation is handled. Furthermore, calibration may also be performed easily by a later optional alignment with world time (actual time), for example, via the PC 4.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A blood glucose system for treating a glucose metabolic disorder, comprising:
   a portable, independent ambulantly operable dosing device for delivering a medicinal agent for the treatment of the glucose metabolic disorder to a body, the dosing device being free from having an integrated time counter for generating relative time values, wherein each relative time value is a time count in relation to a reference instant and is not an actual time, a memory unit in which data sets of dosing quantities and relative time values are stored, and a device for transmitting stored data sets to a data processing apparatus;

a portable, independent ambulantly operable blood glucose measuring device for determining a blood glucose content of the body, the blood glucose measuring device including an integrated time standard, a memory unit in which data sets of blood glucose measurements and associated time values are stored, and a device for transmitting stored data sets to a data processing apparatus; and wherein the data processing apparatus is for processing data sets of the dosing device and the blood glucose measuring device, the data processing apparatus having a receiving device for receiving the data sets from the dosing device and the blood glucose measuring device, wherein the data processing device has an arithmetic unit for converting the relative time values of the data sets of the dosing device into absolute time values by calculating a difference between the relative time value of the time counter of the dosing device and the associated time value of the time standard of the blood glucose measuring device;

wherein, the data processing apparatus synchronizes the data sets of the dosing device and the data sets of the blood glucose measuring device with one another by adding the difference to the relative time value of the time counter of the dosing device;

wherein the dosing device has a needle and a needle sensor with which it registers whether the needle is in the body during delivery of the medicinal agent, and further operates in a priming mode to evaluate when a bolus is delivered without the needle being injected in the body and marks the data sets accordingly when the bolus is delivered without the needle being injected in the body.

2. The system of claim 1, wherein the relative time values of the time standard of the blood glucose measuring device are used as time values for linking the data sets of the dosing device and the blood glucose measuring device.

3. The system of claim 1, wherein the data processing apparatus further comprises an integrated time standard, and wherein the associated time values of the time standard of the blood glucose measuring device or time values of the time standard of the data processing apparatus are used as time values for linking the data sets of the dosing device and the blood glucose measuring device.

4. The system of claim 1, wherein the dosing device is further defined as an insulin pen.

5. The system of claim 1, wherein transmission of the data sets from the blood glucose measuring device or the dosing device to the data processing apparatus is performed using a cable connection or wirelessly.

6. The system of claim 1, wherein the data processing apparatus comprises a conversion unit which converts relative time values of the time counter of the dosing device into clock times.

7. A method for processing analysis results using a blood glucose system for treating a glucose anabolic disorder, the blood glucose system comprising a dosing device for delivering a medicinal agent for a treatment of the glucose anabolic disorder to a body, the dosing device being free from having an integrated time standard and including an integrated time counter for generating relative time values, wherein each relative time value is a time count in relation to a reference instant and is not an actual time, a memory unit in which data sets of dosing quantities and relative time values are stored, and a device for transmitting stored data sets to a data processing apparatus, a blood glucose measuring device for determining blood glucose content of the body, wherein the blood glucose measuring device comprises an integrated time standard, a memory unit in which data sets of blood glucose measurements and associated time values are stored, and a device for transmitting stored data sets to the data processing apparatus, and a data processing apparatus for processing data sets of the dosing device and the blood glucose measuring device and having a receiving device for receiving the data sets from the dosing device and the blood glucose measuring device and an arithmetic unit for converting the relative time values of the data sets of the dosing device into absolute time values, wherein the data processing apparatus is implemented to synchronize the data sets of the dosing device and the data sets of the blood glucose measuring device with one another, the method comprises:

storing one or more data sets of deliveries of the medicinal agent for the treatment of the glucose anabolic disorder in the dosing device, the data sets comprising dosing quantities and the relative time values which were obtained using the integrated time counter at an instant of a particular delivery;

storing one or more data sets of blood glucose measurements in the blood glucose measurement device, the one or more data sets containing analysis results and the associated time values obtained from using the integrated time standard at an instant of each measurement, transmitting one or more data sets of the blood glucose measuring device and one or more data sets of the dosing device to the data processing apparatus and transferring a current relative time value of the time counter of the dosing device to the data processing apparatus;

calculating the absolute time values at which the medicinal agent was delivered by the dosing device using the data processing apparatus from the relative time values of the data set of the dosing device by calculating a difference between the current relative time value of the time counter of the dosing device and a current associated time value of the time standard of the blood glucose measuring device and adding the difference to the relative time values of the dosing device; and processing the dosing quantities and analysis results based on the calculated absolute time values, such that the associated time values of the blood glucose measuring device are used as the time values for linking the data sets of the dosing device and the blood glucose measuring device wherein the dosing device has a needle and a needle sensor with which it registers whether the needle is in the body during delivery of the medicinal agent and further operates in a priming mode to evaluate when a bolus is delivered without the needle being injected in the body and marks the data sets accordingly when the bolus is delivered without the needle being injected in the body.

8. The method of claim 7, wherein the data processing apparatus further comprises an integrated time standard and wherein the time values of the time standard of the blood glucose measuring device or the data processing apparatus are used as the time standard for synchronizing and linking the data sets of the dosing device and the blood glucose measuring device.

9. The method of claim 7, wherein, when stored data sets are transmitted from the dosing device to the data processing apparatus, the time difference between the time counter of the dosing device and the time standard is ascertained and the ascertained time difference is used immediately or at a later instant for correcting the relative time values of the data sets of the dosing device.

10. The method of claim 7, wherein, upon a first data transmission, a first time difference between the time standard and time counter is ascertained, and upon a subsequent second data transmission a corresponding second time difference is ascertained, such that time values lying between the first and second data transmissions are ascertained by interpolating between the first and second time differences and adding the interpolated time difference to the relative time values of the dose delivery.

11. The method of claim 7, wherein the step of processing dosing quantities and analysis results further comprises storing the one or more data sets of the dosing device and displaying the one or more data sets of the dosing device.

12. The method of claim 7, wherein the time counter counts using a predefined pulse rate and the calculation of the relative time values is calculated from the formula $tA=tD-(nD-nA)/v$.

13. The method of claim 7, wherein a duration of a dosing delivery is registered in a given data set stored by the dosing device, such that a beginning and an end of a dosing delivery is marked in the given data set of the dosing device at associated time values.

* * * * *